(12) United States Patent
Gumaste

(10) Patent No.: US 7,810,495 B2
(45) Date of Patent: *Oct. 12, 2010

(54) PACKAGING AND DELIVERY OF PHARMACEUTICALS AND DRUGS

(75) Inventor: Anand V. Gumaste, Princeton Junction, NJ (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 221 days.

This patent is subject to a terminal disclaimer.

(21) Appl. No.: 11/425,097

(22) Filed: Jun. 19, 2006

(65) Prior Publication Data

US 2006/0237011 A1    Oct. 26, 2006

Related U.S. Application Data

(63) Continuation of application No. 09/888,837, filed on Jun. 25, 2001, now Pat. No. 7,080,644.

(60) Provisional application No. 60/214,578, filed on Jun. 28, 2000.

(51) Int. Cl.
   A61M 15/08   (2006.01)
   A61M 16/00   (2006.01)
   A61M 15/00   (2006.01)
   A61M 11/00   (2006.01)
   F16K 31/02   (2006.01)

(52) U.S. Cl. .................... 128/203.23; 128/203.21; 128/203.15; 128/203.16; 128/203.12; 128/203.22; 128/200.23; 128/204.21; 128/204.22

(58) Field of Classification Search ............ 128/203.23, 128/203.21, 203.15, 203.16, 203.12, 203.22, 128/200.23, 204.21, 204.22
See application file for complete search history.

(56) References Cited

U.S. PATENT DOCUMENTS

| 2,517,482 A | 8/1950 | Hall | 128/206 |
|---|---|---|---|
| 3,367,535 A | 2/1968 | Gilman et al. | 221/71 |
| 3,410,450 A | 11/1968 | Fortenberry | 221/7 |
| 3,507,277 A | 4/1970 | Altounyan et al | 128/208 |
| 3,518,992 A | 7/1970 | Altounyan et al | 128/208 |
| 3,635,219 A | 1/1972 | Altounyan et al | 128/266 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A | 4/1976 | Wilke et al. | 128/266 |
| 4,072,249 A | 2/1978 | Ekenstam et al. | 222/95 |
| 4,733,797 A | 3/1988 | Haber | 221/8 |
| 5,207,217 A | 5/1993 | Cocozza et al. | 128/203.21 |
| 5,284,133 A | 2/1994 | Burns et al. | 128/200.23 |
| 5,349,947 A | 9/1994 | Newhouse et al. | 128/203.21 |
| 5,458,135 A | 10/1995 | Patton et al. | 128/200.14 |
| 5,492,112 A | 2/1996 | Mecikalski et al. | 128/203.15 |
| 5,544,646 A | 8/1996 | Lloyd et al. | 128/200.14 |
| 5,694,920 A * | 12/1997 | Abrams et al. | 128/200.16 |

(Continued)

FOREIGN PATENT DOCUMENTS

GB    2264237    8/1993

*Primary Examiner*—Patricia M Bianco
*Assistant Examiner*—Nihir Patel
(74) *Attorney, Agent, or Firm*—Hayes Soloway P.C.

(57) ABSTRACT

A blister pack for use with inhalation therapy inhalers comprises an elongate bottom element having an overlying top element defining a plurality of spaced top crowned areas containing powder or liquid medications or drugs.

14 Claims, 2 Drawing Sheets

U.S. PATENT DOCUMENTS

| | | | | |
|---|---|---|---|---|
| 5,699,789 A | 12/1997 | Hendricks | ............... | 128/203.15 |
| 5,823,183 A | 10/1998 | Casper et al. | ........... | 128/203.15 |
| 5,873,360 A | 2/1999 | Davies et al. | ........... | 128/203.15 |
| 5,881,719 A | 3/1999 | Gottenauer et al. | .... | 128/203.15 |
| 5,921,237 A * | 7/1999 | Eisele et al. | ............ | 128/203.21 |
| 5,944,012 A | 8/1999 | Pera | ...................... | 128/203.15 |
| 6,026,809 A | 2/2000 | Abrams et al. | ......... | 128/203.15 |
| 6,029,663 A | 2/2000 | Eisele et al. | ............ | 128/203.21 |
| D421,800 S | 3/2000 | Doat | ......................... | D24/110 |
| 6,032,666 A | 3/2000 | Davies et al. | ........... | 128/203.15 |
| 6,142,146 A | 11/2000 | Abrams et al. | ......... | 128/203.15 |
| 6,152,130 A | 11/2000 | Abrams et al. | ......... | 128/204.21 |
| 6,209,538 B1 | 4/2001 | Casper et al. | ........... | 128/203.15 |
| 6,312,909 B1 | 11/2001 | Shyjan | ........................ | 435/6 |
| 6,415,790 B1 | 7/2002 | Leedom et al. | ........ | 128/203.15 |
| 6,536,427 B2 | 3/2003 | Davies et al. | ........... | 128/203.15 |
| 6,543,442 B2 | 4/2003 | Gonda et al. | ............ | 128/200.14 |
| 6,698,425 B1 | 3/2004 | Widerstrom | ............ | 128/203.25 |
| 6,792,945 B2 | 9/2004 | Davies et al. | ........... | 128/203.15 |
| 6,871,647 B2 | 3/2005 | Allan et al. | ............. | 128/203.21 |
| 6,889,690 B2 | 5/2005 | Crowder et al. | ........ | 128/203.15 |
| 6,962,266 B2 | 11/2005 | Morgan et al. | ................. | 221/25 |
| 6,971,383 B2 | 12/2005 | Hickey et al. | ........... | 128/203.15 |

* cited by examiner

PACKAGING AND DELIVERY OF PHARMACEUTICALS AND DRUGS

The present application is a continuation of U.S. patent application Ser. No. 09/888,837, filed Jun. 25, 2001, now U.S. Pat. No. 7,080,644, which claims priority from U.S. Provisional Application Ser. No. 60/214,578, filed Jun. 28, 2000.

FIELD OF THE INVENTION

The present invention relates generally to the field of metering, packaging and delivery of pharmaceuticals and drugs. Particular utility for the present invention is found in the area of facilitating metering and packaging of medications and drugs for inhalation therapy and will be described in connection with such utilities, although other utilities are contemplated, including liquid medication applications.

DISCUSSION OF THE PRIOR ART

Certain diseases of the respiratory tract are known to respond to treatment by the direct application of therapeutic agents. As these agents are most readily available in dry powdered form, their application is most conveniently accomplished by inhaling the powdered material through the nose or mouth. This powdered form results in the better utilization of the medication in that the drug is deposited exactly at the site desired and where its action may be required; hence, very minute doses of the drug are often equally as efficacious as larger doses administered by other means, with a consequent marked reduction in the incidence of undesired side effects and medication cost. Alternatively, the drug in this form may be used for treatment of diseases other than those of the respiratory system. When the drug is deposited on the very large surface areas of the lungs, it may be very rapidly absorbed into the blood stream; hence, this method of application may take the place of administration by injection, tablet, or other conventional means.

It is the opinion of the pharmaceutical industry that the bioavailability of the drug is optimum when the drug particles delivered to the respiratory tract are between 1 to 5 microns in size. When the drug particles need to be in this size range the dry powder delivery system needs to address a number of issues:

(1) Small size particles develop an electrostatic charge on themselves during manufacturing and storage. This causes the particles to agglomerate or aggregate, resulting in clusters of particles which have an effective size greater than 5 microns. The probability of these large clusters making it to the deep lungs then decreases. This in turn results in a lower percentage of the packaged drug being available to the patient for absorption.

(2) The amount of active drug that needs to be delivered to the patient may be of the order of 10s of micrograms. For example, albuterol, in the case of a drug used in asthma, this is usually 25 to 50 micrograms. Current manufacturing equipment can effectively deliver aliquots of drugs in milligram dose range with acceptable accuracy. So the standard practice is to mix the active drug with a filler or bulking agent such as lactose. This additive also makes the drug "easy to flow". This filler is also called a carrier since the drug particles also stick to these particles through electrostatic or chemical bonds. These carrier particles are very much larger than the drug particles in size. The ability of the dry powder inhaler to separate drug from the carrier is an important performance parameter in the effectiveness of the design.

(3) Active drug particles with sizes greater than 5 microns will be deposited either in the mouth or throat. This introduces another level of uncertainty since the bioavailability and absorption of the drug in these locations is different from the lungs. Dry powder inhalers need to minimize the drug deposited in these locations to reduce the uncertainty associated with the bioavailability of the drug.

Prior art dry powder inhalers (DPIs) usually have a means for introducing the drug (active drug plus carrier) into a high velocity air stream. The high velocity airstream is used as the primary mechanism for breaking up the cluster of micronized particles or separating the drug particles from the carrier. Several inhalation devices useful for dispensing this powder form of medication are known in the prior art. For example, in U.S. Pat. Nos. 3,507,277; 3,518,992; 3,635,219; 3,795,244; and 3,807,400, inhalation devices are disclosed having means for piercing or removing the top of a capsule containing a powdered medication, which upon inhalation is drawn out of the pierced or topped capsule and into the user's mouth. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, a device is disclosed having a powder containing capsule placed in a lower chamber before inhalation, where it is pierced by manual depression of a piercing pin by the user. After piercing, inhalation is begun and the capsule is drawn into an upper chamber of the device where it moves about in all directions to cause a dispensing of powder through the pierced hole and into the inhaled air stream. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

These prior art devices present several problems and possess several disadvantages which are remedied by the inhalation devices of the present invention. For instance, these prior art devices require that the user exert considerable effort in inhalation to effect dispensing or withdrawal of powder from a pierced capsule into the inhaled air stream. With these prior art devices, suction of powder through the pierced holes in the capsule caused by inhalation generally does not withdraw all or even most of the powder out of the capsule, thus causing a waste of the medication. Also, such prior art devices may result in uncontrolled amounts or clumps of powdered material being inhaled into the user's mouth, rather than a constant inhalation of controlled amounts of finely dispersed powder.

The above description of the prior art is taken largely from U.S. Pat. No. 3,948,264 to Wilke et al, who disclose a device for facilitating inhalation of a powdered medication that includes a body portion having primary and secondary air inlet channels and an outlet channel. The secondary inlet channel provides an enclosure for a capsule containing the powdered medication and the outlet channel is formed as a mouthpiece protruding from the body. A capsule piercing structure is provided, which upon activation forms one or more holes in the capsule so that upon vibration of the capsule by an electro-mechanical vibrator, the powdered drug may be released from the capsule. The piercing means disclosed in Wilke et al includes three radially mounted, spring-biased piercing needles mounted in a trochoidal chamber. Upon hand rotation of the chamber, simultaneous inward radial motion of the needles pierces the capsule. Further rotation of the chamber allows the needles to be retracted by their spring mountings to their original positions to withdraw the needles from the capsule. The electromechanical vibrator includes, at its innermost end, a vibrating plunger rod which projects into the intersection of the inlet channel and the outlet channel. Connected to the plunger rod is a mechanical solenoid buzzer for energizing the rod to vibrate. The buzzer is powered by a high energy electric cell and is activated by an external button switch. According to Wilke et al, upon inhalation through outlet channel 3 and concurrent pressing of switch 10d to activate the electromechanical vibrating means 10, air is sucked through inlet channels 4 and 12 and the air stream through the secondary inlet channel 4 raises the capsule up against the vibrating plunger rod 10a. The capsule is thus vibrated rapidly with powder being fluidized and dispensed from the pierced holes therein. (This technique is commonly used in manufacturing for dispensing powder through a hopper where the hopper is vibrated to fluidize the powder and move it through the hopper outlet. The pierced holes in the capsule represent the hopper outlet.) The air stream through inlet channel 4 and 12 aids in withdrawal of powder from the capsule and carries this powder through the outlet channel 3 to the mouth of the user. (Wilke et al, column 3, lines 45-55). Wilke et al further discloses that the electromechanical vibrator means may be placed at a right angle to the inlet chamber and that the amplitude and frequency of vibration may be altered to regulate dispensing characteristics of the inhaler.

Thus, as noted above, the vibrator in Wilke et al's disclosed inhaler is an electromechanical device consisting of a rod driven by a solenoid buzzer. (This electromechanical means may be a motor driving a cam [Col. 4, Line 40]). A disadvantage of the inhaler implementation as disclosed by Wilke is the relatively large mechanical movement required of the rod to effectively vibrate the capsule. The large movement of the rod, usually around 100s of microns, is necessary due to the elasticity of the capsule walls and inertia of the drug and capsule.

Moreover, solenoid buzzers typically have operating frequencies less than 5 Khz. This operating frequency tends to be noisy and therefore is not desirable when incorporated into a dry powder inhaler from a patient's perspective. A further disadvantage of the electrochemical actuators of Wilke is the requirement for a high energy source (Wilke et al, Col. 3, line 38), thus requiring a large battery source or frequent changes of the battery pack for portable units. Both these features are not desirable from a patient safety and "ease of use" standpoint.

The inhaler of Wilke et al is primarily intended to reduce the amount of powder left behind in the capsule relative to other inhalers cited in the patent disclosure. (Wilke et al, Col. 4, lines 59-68, Col. 5, lines 1-48). However, Wilke et al does not address the need to deaggregate the powder into particle sizes or groups less than 5 microns in size as is required for effective delivery of the medication to the lungs; rather Wilke et al, like the prior art inhalers continues to rely on the air stream velocity to deaggregate the powder ejected into the air stream, into particle sizes suitable for delivery to the lungs.

Another prior art inhalation device is disclosed in Burns et al U.S. Pat. No. 5,284,133. In this device, a liquid medication is atomized by an ultrasonic device such as a piezo element (Burns et al, Col. 10, lines 36-51). A stream of air, usually at a high velocity, or a propellant then carries the atomized particles to the patient. The energy required to atomize the liquid medication in the nebulizer is prohibitively high, making this approach for the delivery of drugs to the lungs only feasible as a desk top unit. The high voltage requirements to drive the piezo, to produce the necessary mechanical displacements, also severely affects the weight and size of the device. It is also not obvious that the nebulizer operating principles can be applied to the dry powder inhalers for delivery or powder medication to the lungs.

The prior art devices therefore have a number of disadvantages which makes them less than desirable for the delivery of dry powder to the lungs. Some of these disadvantages are:

The performance of the prior art inhalers depends on the flow rate generated by the user. Lower flow rate does not result in the powder being totally deaggregated and hence adversely affects the dose delivered to the patient.

Inconsistency in the bioavailability of the drugs from dose-to-dose because of lack of consistency in the deaggregation process.

Large energy requirements for driving the electromechanical based inhalers which increases the size of the devices making them unsuitable for portable use.

Loss of medication from opened or topped capsules.

Deterioration of medication in open or topped capsules due to exposure to oxygen or moisture.

In my prior U.S. Pat. Nos. 6,026,809 and 6,142,146 (with Abrams), we provide an inhaler that utilizes vibration to facilitate suspension of a medication or drug into a gas that overcomes the aforesaid and other disadvantages and drawbacks of the above prior art. More particularly, the inhaler of our aforesaid patent includes a piezoelectric vibrator for vibrating the medication or drug. In a preferred embodiment of our aforesaid '809 and '146 patents, the medication or drug is supplied from a coiled tape having a plurality of spaced blisters or wells for carrying controlled aliquots of a dry powder medication or drug.

Referring to FIG. 1 which corresponds to FIG. 9 of our aforesaid '809 U.S. patent, the medication or drug is packaged in a disposable drug cartridge 210 which includes a coiled tape 218 carrying a plurality of spaced flat walled blisters or wells 220 for containing controlled aliquots medication. A release film 221 covers and seals blisters or wells 220. Tape 218 is formed as a coil, and threaded between a first guide platen 222 and pinch roller 224. Pinch roller 224 in turn is driven by a take-up spool 226 which in turn is driven by a thumbwheel 228 which is mounted on a common shaft with the take-up spool 226. In use, release film 221 is peeled from the tape 218, whereby to open blisters or wells 220, one at a time, as the film is advanced through the cartridge, and the release film 221 is collected on take-up spool 226.

Completing cartridge 210 is a piezoelectric element 232 for mechanically engaging the bottom wall of the opened blisters or wells 220, one at a time, as they are selectively advanced in position over and in contact with the piezoelectric element 232. Tape 218 also preferably includes detent means or the like for indexing the tape so that a selected opened blister or well 220 is automatically positioned over piezoelectric element 232. Finally, an actuating circuit and power supply (not shown) is mounted within cartridge 210.

Preferably, but not necessarily, the interior walls of the housing are coated with a metallized coating 234 so as to obviate possible electrostatic charge buildup within the housing.

Also, if desired, an auxiliary air inlet 236 may be provided immediately upstream of the piezoelectric element 232 for assisting in carrying particles as they are energized by the piezoelectric element.

BRIEF DESCRIPTION OF THE INVENTION

The present invention provides an improvement over the medication packaging and delivering technology described in our aforesaid '809 and '146 patents. More particularly, in accordance with the present invention, controlled aliquots or doses of a medication or drug are pre-packaged in a blister pack. The blister pack includes a frangible crowned top element which may be conical, conical with a rounded point, rounded, or other raised shape configuration, and a bottom element which may be a flat web or membrane, or which itself may be of shaped configuration, e.g. conical, round, dish shaped, etc. for closely engaging with an underlying piezo element. The shape and size of the blisters is chosen to provide optimum controlled delivery of controlled amounts of controlled size particles of a given medication or drug. Before being delivered, the top element of the blister pack is pierced with a piercing device such as a sharp needle to form one or more apertures for delivery of the medication or drug contained within the blister pack. The hole pattern and hole size is selected to provide optimization of delivery of the particular medication or drug packaged therein. The holes also may act as filters whereby to prevent ejection from the blisters of aggregated or agglomerated particles, until the particles are broken up to optimal size by energy input from the piezo. Thus, in the case, e.g. of a dry powder medication or drug or a liquid medication or drug, particle size and dose of the medication or drug delivered can be optimized, and tailored to the frequency of the piezo. Typically, the bottom blister element is placed on/in close proximity to the piezo prior to or contemporaneously with piercing the top element. The top element is pierced, and activation of the piezo drives the medication or drug from the blister pack through the perforations in the top element.

BRIEF DESCRIPTION OF THE DRAWINGS

Other features and advantages of the present invention will be seen from the following detailed description, taken in conjunction with the accompanying drawings, wherein.

DETAILED DESCRIPTION OF THE PRESENT INVENTION

Figure 1A:
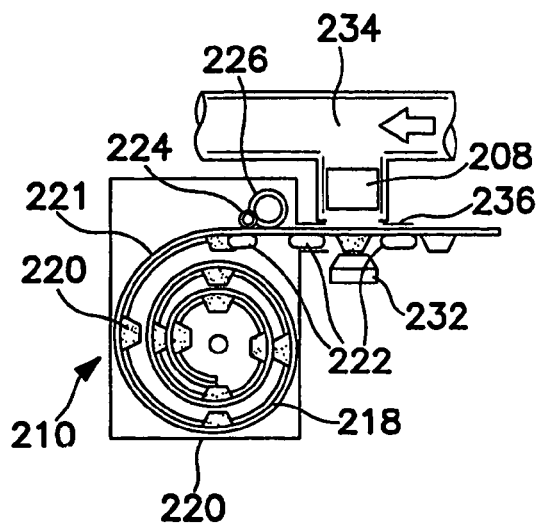
FIGS. 1a and 1b are schematic representations of a dry powder packaging and delivery system in accordance with the prior art.
Figure 1B:
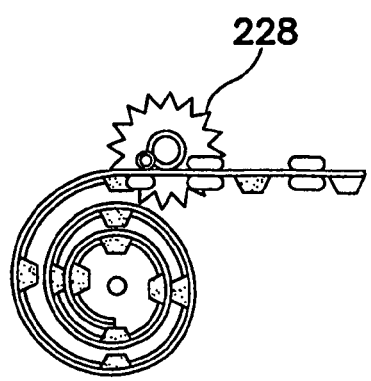
Figure 2:
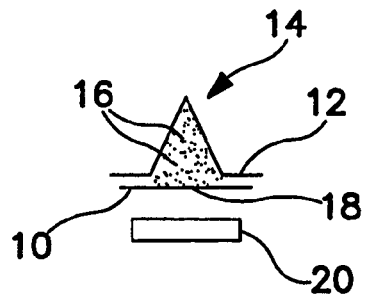
FIGS. 2-5 illustrate various blister packs made in accordance with the present invention.

Referring to FIG. 2, a blister pack in accordance with the present invention comprises a bottom element 10 in the form of an elongate plastic tape or other flexible material, e.g. cloth, foil, paper, etc., having an overlying top element 12, carrying a plurality of spaced top crowned areas 14 containing controlled aliquots or doses of a dry powder medication or drug or a liquid medication or drug. As illustrated in FIG. 2, the top crowned areas 14 are shaped as inverted cones and are mounted to bottom element 10 in regular spaced intervals. Areas 14 are substantially completely filled with a controlled aliquot or dose of a powder or liquid medication or drug. Typically, the blister pack of the present invention is provided as coil or a circular cartridge or unit dose pack. In use, the blister pack is uncoiled and advanced to a puncture stage where one or a plurality of controlled size holes 16 are punched through the top wall of the top crowned area 14.

The top crown areas 14 and bottom element 10 form an enclosed volume. The shape, height and volume of the blister pack, together with the size and number of holes punched through the top crowned area 14, play an important role in the de-aggregation and aerosolization of the powder or liquid material in the blister pack.

The three main phenomenon, besides others, which help in the de-aggregation and aerosolization of the material in the blister, are the Helm-Holtz resonator, the standing waves set-up in the blister pack and the vibrator frequency of the piezo. The Helm-Holtz resonator is formed by the holes punches in the top crown and the volume of the blister pack. The Helm-Holtz resonator helps to de-aggregate and eject the material from the blister pack. The frequency of the resonator will have to be optimized for maximum material de-aggregation and ejection efficiency.

The standing waves in the blister pack are determined by the height and shape of the blister. The standing waves help to lift and aerosolize the material in the blister. The standing wave frequency is determined by the height and shape of the blister pack and will have to be optimized for maximum de-aggregation of the material in the blister.

The third main phenomenon is the piezo vibrator frequency. The piezo frequency should be such as to excite the Helm-Holtz resonator and establish the standing waves in the blister pack. The interface of the element 10 with the piezo vibrator should be such as to provide maximum coupling of the piezo vibrator energy into the blister pack.

It will be appreciated by those skilled in the art that these three phenomenon need to be optimized individually or in combination to achieve maximum de-aggregation and aerosolization of the powder or liquid material in the blister pack to make it suitable for delivery of medication or other compounds to the lungs.

The tape is advanced so that that area 18 of the bottom portion underlying the punctured top crowned area 14 is in contact with or adjacent the piezoelectric element 20. The piezoelectric element 20 is then energized and couples with area 18, causing the blister pack to vibrate whereby to deaggregate and drive the powdered or liquid medication or drug out of the blister pack through holes 16.

Figure 3:
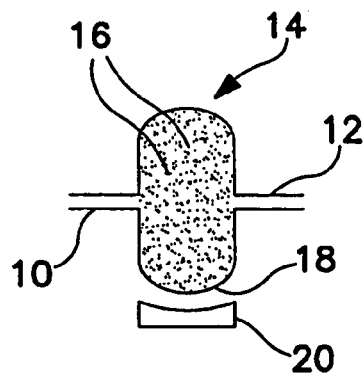
Figure 4:
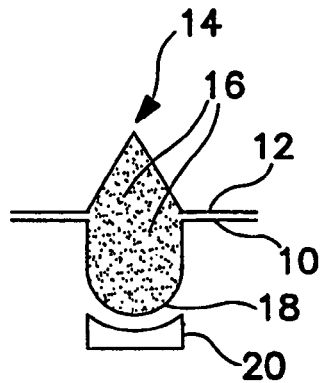
Figure 5:
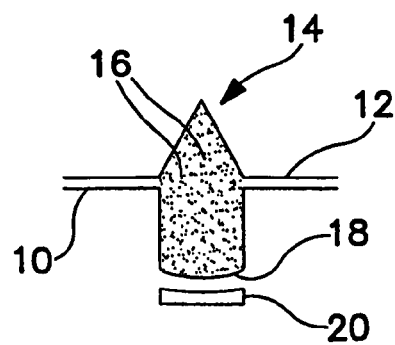

Other shapes of blister packs made in accordance with the invention are shown in FIGS. 3-5, and may include domed blister packs as illustrated in FIG. 3, dome/cone combinations as shown in FIG. 4, and cone/pill box combinations as shown in FIG. 5. In all cases the lower element should be flat or nearly flat or at least have a generally flattened or slightly rounded surface for interfacing or coupling with the piezo.

A particular feature and advantage of the present invention is that the blister pack, when coupled to the piezo essentially acts as a miniature pump which expels the powder or liquid into the air stream.

Figure 6A:
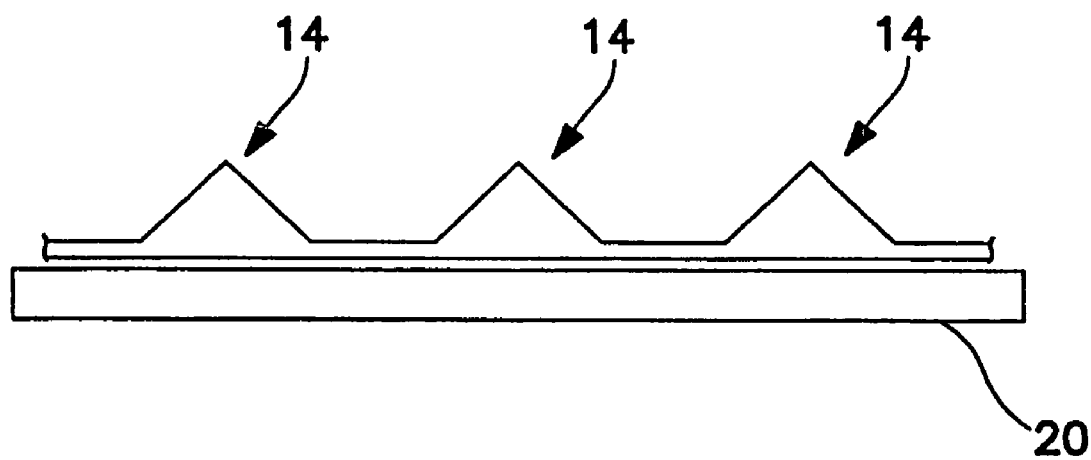
FIGS. 6A and 6B illustrate a plurality of blister packs and piezos in accordance with another embodiment of the invention.
Figure 6B:
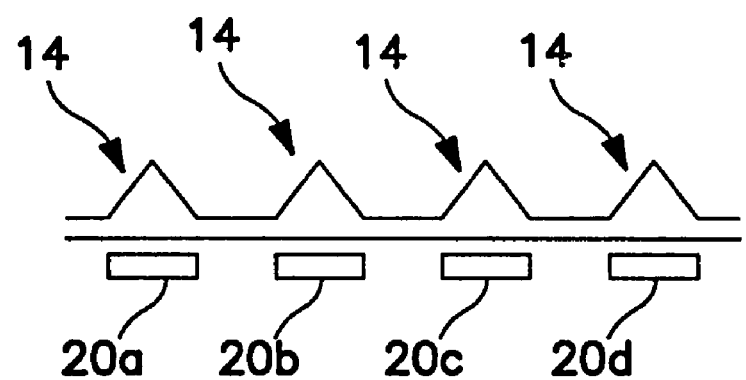

The present invention offers several other advantages over the prior art. For one, the blister pack keeps the powdered or liquid medications or drugs freshly sealed and dry until just prior to use. Also, the blister pack keeps the powdered or liquid medications or drugs from flowing out or being lost, and allows the inhaler to be used in any orientation. Additionally, the size and shape of the top and bottom blister pack elements can be tuned to specific drug/piezo combinations for optimizing medication or drug delivery. Also, dosage size can be adjusted simply by changing the number of blister packs opened in the air channel. In such case, the multiple blisters may be opened simultaneously and driven by a common or by multiple piezos 20a, 20b . . . (see FIGS. 6A and 6B), or sequentially. Also, if desired, two or more piezos may be employed, e.g. adjacent the bottom and sides of the blisters, and activated simultaneously or sequentially. Another advantage as noted supra is that the holes in the blister pack serve as a filter or sieve so as to prevent expulsion from the blister pack of aggregated or oversize particles. Thus, overdosing and/or waste is eliminated.

Various changes may be made in the foregoing without departing from the spirit and scope of the invention. For example, the blister pack of the present invention advantageously may be employed for packaging and delivery of other wet or dry materials including, for example, vitamins, hormones, steroids and other bioactive small molecules, peptides, proteins, etc.

The invention claimed is:

1. A blister pack for use with inhalation therapy inhalers equipped with a vibratory de-aggregator, comprising a first element having spaced areas for interfacing and coupling with an inhaler vibratory de-aggregator, and a frangible second element overlying the first element and forming spaced top crowned areas shaped as upright cones defining a volume located over said first element spaced areas, and containing powder or liquid material, wherein, upon puncture of the frangible second element to form at least one puncture hole with an area smaller than the spaced top crown area, the volume of the blister pack and the at least one puncture hole form a standing wave or Helm-Holtz resonator whereby contents of the blister are forcibly ejected from the blister through the puncture holes in the frangible second element when the spaced areas are interfaced coupled with a vibratory de-aggregator.

2. A blister pack according to claim 1, wherein said first element comprises an elongate flexible tape.

3. A blister pack for use with inhalation therapy inhalers equipped with a vibratory de-aggregator, comprising a first element having spaced areas for interfacing and coupling with an inhaler vibratory de-aggregator, and a frangible second element overlying the first element and forming spaced top crowned areas shaped as inverted domes defining a volume located over said first element spaced areas, and containing powder or liquid material, wherein, upon puncture of the frangible second element to form at least one puncture hole with an area smaller than the spaced top crown area the volume of the blister pack and the at least one puncture hole form a standing wave or Helm-Holtz resonator whereby contents of the blister are forcibly ejected from the blister through the puncture holes in the frangible second element when the spaced areas are interfaced coupled with a vibratory de-aggregator.

4. A blister pack according to claim 1, wherein the first element includes a depression opposite the top crowned areas.

5. A blister pack according to claim 4, wherein the depression is shaped as an inverted dome.

6. A blister pack according to claim 4, wherein the depression is shaped as an inverted pill box.

7. A blister pack according to claim 1, wherein said material comprises a medication.

8. A blister pack according to claim 1, wherein said material comprises a vitamin.

9. A blister pack according to claim 1, wherein said material comprises a hormone.

10. A blister pack according to claim 1, wherein said material comprises a steroid.

11. A blister pack according to claim 1, wherein said material comprises a bioactive material.

12. A blister pack according to claim 1, wherein a size and number of puncture holes together with volume formed by the blister pack are optimized for de-aggregation and aerosolization of material in the blister pack.

13. A blister pack according to claim 1, wherein a height and shape of the blister pack is optimized for de-aggregation and aerosolization of material in the blister pack.

14. A blister pack according to claim 1, wherein an interface to the vibrator is optimized for optimum coupling of the energy into the blister pack for de-aggregation and aerosolization of material in the blister pack.

* * * * *